United States Patent [19]

McRae

[11] Patent Number: Plant 5,994

[45] Date of Patent: May 19, 1987

[54] ASIATIC LILY PLANT NAMED "OREGLOW"

[75] Inventor: Edward A. McRae, Boring, Oreg.

[73] Assignee: Melridge Inc., Gresham, Oreg.

[21] Appl. No.: 772,159

[22] Filed: Sep. 3, 1985

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Charles W. Rummler; John B. Lungmus

[57] ABSTRACT

A new variety of hybrid lily plant bearing clusters of many large flowers particularly characterized by their rich yellow-orange melon color tone and lack of spotting, as well as by their unusually large size, which features are completely new in the upright Asiatic division of lilies suited to forcing and to mass commercial cultivation. The flowers of this new plant are of excellent form, strong color and long persistence, both on the plant and as cut flowers. The plant is an excellent garden plant having high resistance to disease and showing high tolerance of virus. The bulbs of this plant may be precooled and forced out of season for cut flower production, the clone being extremely vigorous and a good grower and propagator.

1 Drawing Figure

BACKGROUND OF THE NEW PLANT

My new variety of lily plant originated as a seedling selected from a group of seedlings resulting from my crossing of the clonal cultivar "Connecticut King" (unpatented) and the clonal cultivar 'Croesus' (unpatented) in the course of breeding efforts carried on by me since 1975 at Sandy, Oreg. with the object of producing spotless upright flowering Asiatic lilies in the shades of yellow and gold and well suited for forcing for out-of-season cut flower production. Also this new lily plant is distinguished by the upright orientation of its unusually large sized flowers and tepal thickness produced profusely on a single stem.

This new variety of lily plant has been asexually reproduced by me and under my direction at Sandy, Oreg., and successive generations produced by bulb scale propagation and natural propagation from bulblets have demonstrated that the novel and distinctive characteristics of my new variety are fixed and hold true under asexual propagation from generation to generation. The resulting clones have shown that this variety possesses the desirable characteristics of hybrid vigor, great hardiness and disease resistance to a high degree and have shown the new plant to be well suited to forcing into flower out of season from bulbs which have been dug at the correct time and properly precooled. October-dug bulbs, properly precooled and potted in January, will flower under glass in western Oregon in an average of 75 to 80 days, with no supplementary lighting and with moderate greenhouse temperatures.

DESCRIPTION OF THE DRAWING

My new variety of lily plant is illustrated by the accompanying photographic drawing, which shows an open bloom illustrating the flower form and tepal arrangement, as well as the distinctive melon color tone of the unspotted flower which has been hand painted to show the true color herein specified.

DESCRIPTION OF THE NEW LILY VARIETY

The following is a detailed description of my new variety of Asiatic hybrid lily, with nomenclature according to The International Lily Register, Second Edition, of The Royal Horticultural Society at London, England, the color designations being according to The R.H.S. Colour Chart of The Royal Horticultural Society published in 1966.

THE PLANT

Origin: Seedling.

Parentage:

*Seed parent.*—Lilium "Connecticut King" (unpatented).

*Pollen parent.*—Lilium 'Croesus' (unpatented).

Classification:

*Horticultural.*—Division I-A, Upright Asiatic Hybrid Lily, according to The Horticultural Classification of Lilies by The Royal Horticultural Society.

*Commercial.*—Asiatic lily cultivar.

Form: Single stem, erect and stately, bearing large clusters of large sized flowers.

Height: About 80 to 90 cm. from bulbs about 15 to 18 cm. in circumference, when light levels are adequate. (Low light levels cause "stretching".).

Growth habit: Vigorous and upright.

Foliage:

*Quantity.*—Abundant.

*Leaf size.*—About 8 to 12 cm. long and about 1 to 2 cm. wide.

*Leaf shape.*—Lanceolate.

*Texture.*—Leathery.

*Aspect.*—Glossy.

*Color.*—Medium green on the upper surface and light green on the lower surface.

Bulbs:

*Size.*'Various, ranging to about 25 cm. in circumference as used commercially.

*Color.*—White.

THE BUD

Form: Long and obtuse ovoid.

Size: About 8 to 9 cm. long and about 5 to 6 cm. in circumference, just prior to opening.

Opening rate: The mature bud opens slowly in response to light; this takes about one hour.

Color: The outside, at the lower tepal surface, is soft green shading into RHS Yellow-Orange, 21-C/D, just prior to opening and as the tepals begin to unfurl.

Peduncle: About 6 to 8 cm. long.

*Character.*—Erect.

*Color.*—Medium green with light plum overlay.

THE FLOWER

Blooming habit: Annually, once and profusely, in mid-season.

Size: The flowers are very large, about 15 to 18 cm. in diameter; the outer tepals being about 2 to 3 cm. wide and the inner tepals being about 3 to 4.5 cm. wide.

Borne: In clusters of about 10 to 14 flowers as a compact raceme on a stem from a bulb 18 to 21 cm. in circumference.

Shape: Flattened cup-shape with tepal tips obtuse and recurved about 180°.

Tepalage:

*Number.*—Six.

*Arrangement.*—Imbricated.

*Appearance.*—Shiny.

*Color.*—The basic color is Yellow-Orange, RHS 23-B, with a deeper flush of Yellow-Orange, RHS 23-A, about 2 cm. wide and 2 cm. long extending from the nectaries. The nectaries are covered with very short white pubescence.

*Spotting.*—None.

*Color change.*—Bright light can bleach the older flowers to RHS 21-B with a flush of 21-A. Cooler temperatures can deepen tepal margins to RHS 23-A.

Fragrance: None.

Lasting quality: The flower is long lasting, both on the plant and as a cut flower. Tepals stay on the stem for about three weeks.

Disease resistance: The flower and plant are resistant to disease and in particular, they are resistant to Fusarium bulb rot and to Botrytis blight as observed in western Oregon.

THE REPRODUCTIVE ORGANS

Stamens:

*Number.*—Six, the arrangement being typical of genus Lilium.

Anthers and pollen:

*Color.*—Grayed Orange, RHS 172-A.

Filaments:

*Length.*—About 5 cm.

*Color.*—RHS 21-D.

Pistils:

*Number.*—One.

*Length.*—About 5 cm.

Stigma:

*Size.*—Large.

*Color.*—Soft Gold, RHS 21-D.

THE FRUIT

Fertility: The fruit is fertile.

Shape: Ovoid.

Color at maturity: Soft brown, sometimes overlaid with soft plum.

This new variety of Asiatic hybrid lily most nearly resembles "Connecticut King" (unpatented) but it has flowers of a more regular and broad-tepalled form, and its color is a soft melon, similar to but deeper than the center stripe of "Connecticut King" (which is otherwise yellow). The new variety has a more regular inflorescence than does "Connecticut King" and it carries only a few secondary buds.

I claim:

1. A new and distinct variety of Asiatic hybrid lily plant substantially as herein shown and described, characterized by its large sized and unique unspotted yellow-orange melon color; the new plant is also distinguished by its vigorous growth and rapid natural propagation, the excellence of its flower form, its high resistance to disease and high tolerance of virus, and its versatility both as a garden plant and as a cut flower produced under glass from precooled bulbs forced out-of-season.

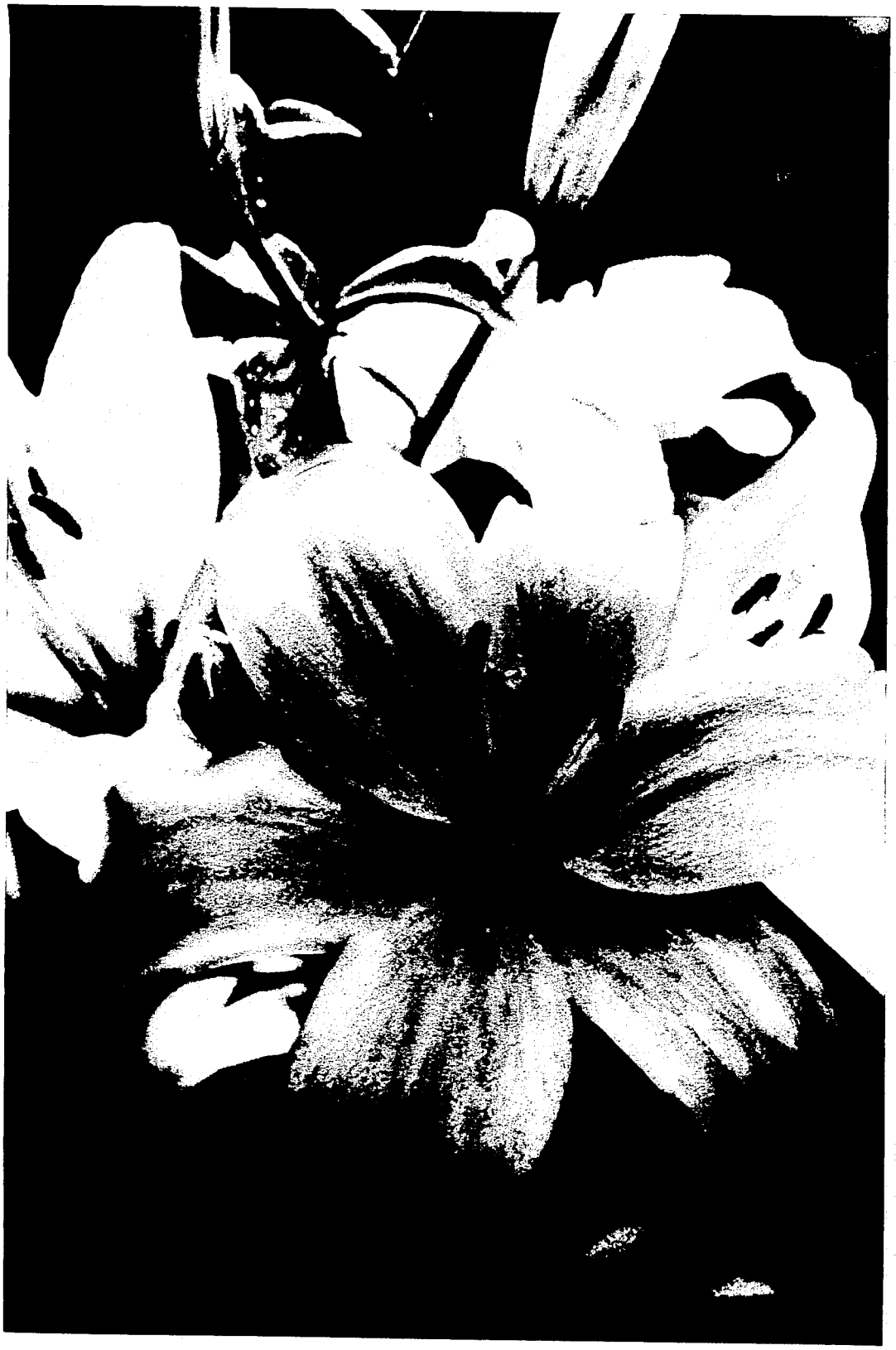

* * * * *